(12) United States Patent
Bass

(10) Patent No.: US 8,821,449 B1
(45) Date of Patent: Sep. 2, 2014

(54) FEEDING TUBE FASTENER

(76) Inventor: Linda Marie Bass, Fort Lauderdale, FL (US)

( * ) Notice: Subject to any disclaimer, the term of this patent is extended or adjusted under 35 U.S.C. 154(b) by 772 days.

(21) Appl. No.: 12/586,373

(22) Filed: Sep. 21, 2009

(51) Int. Cl.
*A61M 5/32* (2006.01)

(52) U.S. Cl.
USPC .......................................... 604/180

(58) Field of Classification Search
USPC ................................. 604/174, 180
See application file for complete search history.

(56) References Cited

U.S. PATENT DOCUMENTS

| | | | |
|---|---|---|---|
| 3,568,679 A * | 3/1971 | Reif ............................. | 604/180 |
| 5,342,330 A * | 8/1994 | Kane et al. ..................... | 604/329 |
| 5,496,283 A * | 3/1996 | Alexander ..................... | 604/180 |
| 5,628,724 A * | 5/1997 | DeBusk et al. ................. | 602/58 |
| 5,795,335 A * | 8/1998 | Zinreich ........................ | 604/174 |
| 6,428,516 B1 * | 8/2002 | Bierman ........................ | 604/174 |
| 2005/0107743 A1 * | 5/2005 | Fangrow, Jr. ............. | 604/164.01 |

* cited by examiner

*Primary Examiner* — Emily Schmidt
(74) *Attorney, Agent, or Firm* — Akerman LLP; Roy P. Zachariah

(57) ABSTRACT

One embodiment of a clear rubber base with two parallel grooves in it attached to a clear rubber lid by a clear rubber base/lid connector. The clear rubber lid has four complementary grooves in it so that when the fastener is closed the grooves from the base and lid line up forming a snug fit for the feeding tube. Attached to the lid and across from the base/lid connector is a clear rubber pull tab. Along the bottom portion of the base is a slit that goes around the entire circumference of the base allowing enough room for the adhesive strip to fit into the slit. With the adhesive strip in place the feeding tube fastener can be applied to the skin of the abdomen.

20 Claims, 3 Drawing Sheets

FEEDING TUBE FASTENER

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND

Medical—Gastroenterology

Prior Art

Hospitals and doctors commonly use silk tape or paper tape to fasten an already implanted feeding tube on to the skin of a patient's abdomen. The silk or paper tape works for a short period of time. However, the tape is not of a permanent nature and needs frequent replacing. The tape is susceptible to dirt and body oils. Many of the patients with feeding tubes are elderly and confused and many of these patients wear diapers. The placement of the feeding tube can also be close to the edges of the diaper. The frequent changing of the different tapes can be irritating to the skin, enhancing skin breakdown. If the tape looses its adhesiveness and the feeding tube becomes loose, it can possibly be exposed to urine and stool. There is also the potential that while the feeding tube is unattached and flopping around it can be accidentally or purposefully pulled out.

Advantages. The advantages of the Feeding Tube Fastener are that it keeps the feeding tube stabilized and prevents it from flopping around. The materials making up the Feeding Tube Fastener are washable and meant for long term use. The fastener itself is clear allowing constant visualization of the feeding tube. The adhesive patch provides a barrier for the skin. It is easy to apply and it is waterproof. It can also be removed without damaging newly formed skin.

SUMMARY

In accordance with one embodiment a feeding tube fastener comprises a clear rubber base having two grooves for the feeding tube to fit into and a notch for the lid to fit into, a clear rubber lid with a gripping aperture adjacent the notch and with a clear rubber pull tab, and an adhesive patch attached to the clear base.

DRAWINGS

Figures

Figure 1:
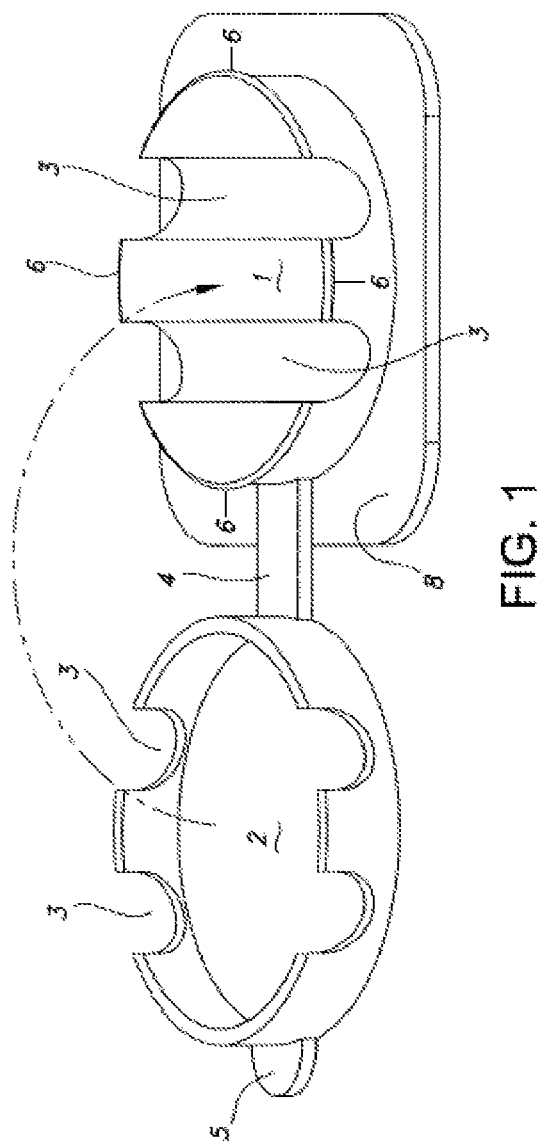
FIG. 1 shows an angled view of the clear rubber base with two grooves in it attached to the clear rubber lid with its adjoining grooves in it in accordance with one embodiment.

REFERENCES NUMERALS 1 base
2 lid
3 groove
4 base/lid connector
5 pull tab
6 gripping aperture

DETAILED DESCRIPTION

First Embodiment

Figure 2:
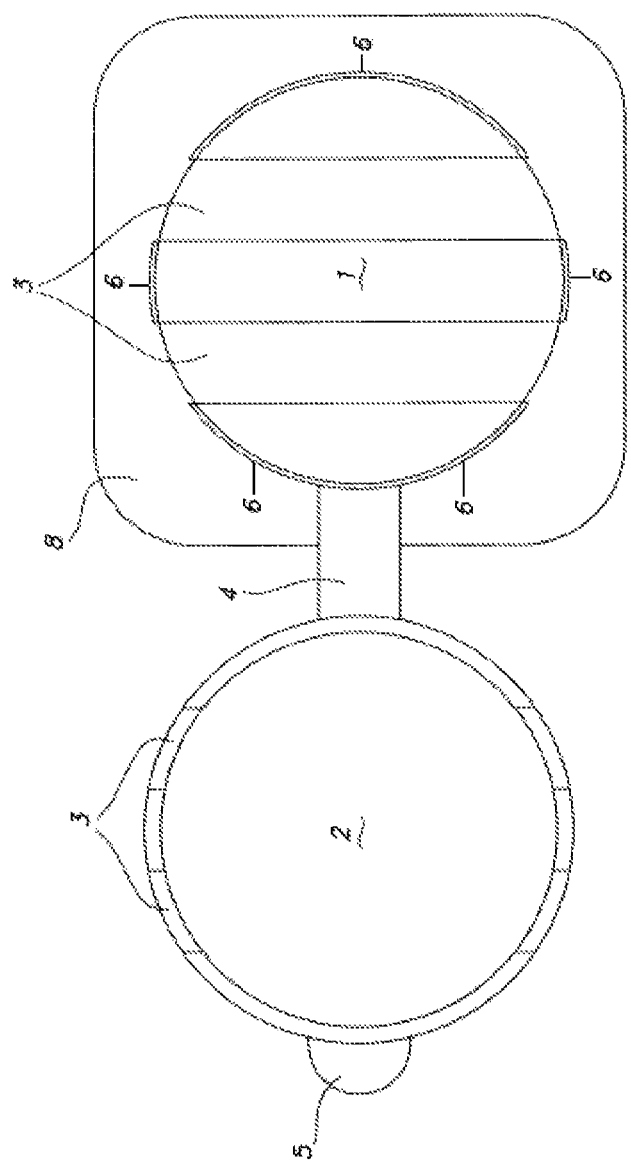
FIG. 2 shows a downward view of the clear rubber base with the clear rubber lid attached to the adhesive contact in accordance with another embodiment.
Figure 3:
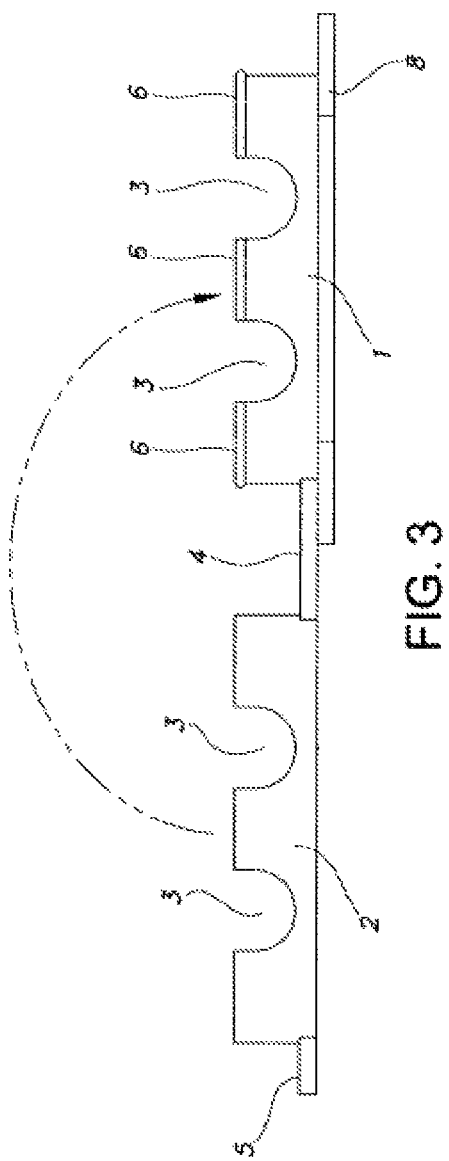
FIG. 3 shows a side view of the clear rubber base attached to the clear rubber lid by a clear rubber base/lid connector in accordance with another embodiment.

One embodiment of the feeding tube fastener is illustrated in FIG. 1 (angled view) and FIG. 2 (downward view). The fastener has a base 1 consisting of clear rubber material with two parallel grooves in it. A feeding tube fits into the grooves and a lid 2 consisting of the same material as the base snaps down over the base holding the feeding tube in place. In the ideal embodiment, the base and lid are a clear silicone rubber but they can consist of any clear flexible rubber that can be repeatedly washed and cleaned.

At one side of the base is a pull tab 5, across from this is a base/lid connector 4. It is here that the lid and base connect. Through the body of the base run two parallel grooves 3 that allow space for the feeding tube while holding it in place. The grooves are at a 90 degree angle from the base lid/connector. At the same 90 degree angle on the lid 3 are four more grooves that line up, when the fastener is closed, with the grooves on the base forming a snug fit for the feeding tube. Running along the upper rim of the base is a gripping aperture 6 initiating a tight fit with the notch when the fastener is closed. Attached to the base is an adhesive strip 8 which is used to attach the fastener to the skin of the abdomen. In the best embodiment, the adhesive strip is a thin polyurethane film.

The base of the fastener is typically a 2¼ in. circle with a height of ½ in. Roughly 1/16 of an inch up from the base is a 1¼ in. slit going around entire circumference of disc in order to accommodate the adhesive strip. The grooves (2 longitudinal grooves located on the base and 4 complementary grooves located on the lid) are ¼ in. wide by ¼ in. deep and are 1 in. apart. The base/lid connector is 1 in. long by ½ in. wide. The lid is roughly a 2⅓ in. circle with a height of ½ in. The pull tab is ½ in. long in the shape of a semi-circle with the flat side attached to the upper edge opposite the base/lid connector. The adhesive strip is approx. 4 in. by 4 in. with rounded edges. There is a 1 in. circle cut out of the middle of the adhesive strip in order to accommodate the base. The edges of the adhesive strip are rounded to discourage nicking caused by clothing or bedding.

One advantage of this embodiment is that it holds the feeding tube in place. It prevents the tube from flopping around and being accidentally pulled out of the stomach. Another advantage of this embodiment is that because the rubber base and lid are clear it allows you to see if any food or formula is remaining in the tube when it is not wanted there.

In the medical field today, a feeding tube is held in place with silk or paper tape. The tape can get dirty or soiled if it is near a wound or diaper. Even body oil can dirty the tape. In order to keep the feeding tube clean the tape has to be replaced frequently, this can cause the skin to breakdown. The adhesive strip holding the embodiment in place is easy to clean with water or soap and water and actually provides a waterproof barrier to the skin. It is easy to apply and can be easily removed without damaging the skin. It is of a more permanent nature and can remain on the skin for a long period of time.

This embodiment also discourages the elderly and sometimes confused patients with a feeding tube from "playing with it" or from pulling it out.

CONCLUSION

This embodiment keeps the feeding tube stable and allows it to remain in a clean environment.

The invention claimed is:

1. A feeding tube fastener for holding a feeding tube in position, the feeding tube fastener comprising:
   a base comprising a pair of grooves configured to receive and hold at least a portion of the feeding tube, wherein the pair of grooves of the base extend across an entire length of the base, wherein the base further comprises a gripping aperture positioned around a circumference of a top surface of the base, wherein a portion of the gripping aperture extends beyond an outermost edge of the base;
   a lid comprising a side wall extending perpendicular to a smooth and flat top surface of the lid, wherein the side wall has a smooth interior and generally cylindrical shape, wherein the side wall includes two pairs of opposing grooves, wherein the two pairs of opposing grooves are parallel to the pair of grooves of the base, wherein the top surface of the lid and the side wall have a circumference such that the side wall fastens to the gripping aperture of the base approximately in a vicinity of an intersection of the side wall and the top surface of the lid when the lid is closed over the base, and wherein the two pairs of opposing grooves of the lid and the grooves of the base are configured to hold the feeding tube when the lid is fastened to the gripping aperture of the base; and
   an adhesive strip connected to a bottom surface of the base of the feeding tube fastener, wherein the adhesive strip is configured to be applied on a user.

2. The feeding tube fastener of claim 1, wherein the lid of the feeding tube fastener comprises a pull tab for pulling the lid towards or away from the base of the feeding tube fastener.

3. The feeding tube fastener of claim 1, wherein the lid is partially connected to the base by utilizing a connector.

4. The feeding tube fastener of claim 1, wherein the base of the feeding tube fastener comprises a clear rubber disc, and wherein the lid of the feeding tube fastener comprises clear rubber.

5. The feeding tube fastener of claim 1, wherein each of the grooves of the pair of grooves of the base are identical, and wherein each groove of the two pairs of grooves of the lid are identical.

6. The feeding tube fastener of claim 3, wherein the pair of grooves of the base and the two pairs of opposing groves of the lid of the feeding tube fastener are perpendicular to the connector.

7. The feeding tube fastener of claim 1, wherein the base and the lid of the feeding tube fastener comprise silicone rubber.

8. The feeding tube fastener of claim 1, wherein the adhesive strip comprises polyurethane film.

9. The feeding tube fastener of claim 1, wherein a middle portion of the adhesive strip is removed from the adhesive strip, wherein the adhesive strip is configured to accommodate the base of the feeding tube fastener at an opening where the middle portion was removed.

10. A feeding tube fastener, comprising:
    a base comprising a pair of parallel grooves configured to receive at least a portion of a feeding tube, wherein the pair of parallel grooves of the base extend across an entire length of the base, wherein the base includes a gripping aperture positioned around an upper rim of the base, wherein a portion of the gripping aperture extends beyond an outermost edge of the base;
    a lid comprising a side wall extending perpendicular to a smooth and flat top surface of the lid, wherein the side wall has a smooth interior and generally cylindrical shape, wherein the side wall includes a plurality of grooves, wherein the plurality of grooves of the lid are parallel to the pair of grooves of the base, wherein the lid is at least partially connected to the base by utilizing a connector, wherein the top surface of the lid and the side wall have a circumference such that the side wall fastens to the gripping aperture approximately in a vicinity of an intersection of the side wall and the top surface of the lid when the lid is closed over the base, and wherein the plurality of grooves of the lid and the grooves of the base are configured to hold the feeding tube when the lid is fastened to the base;
    and an adhesive strip connected the bottom surface of the base of the feeding tube fastener.

11. The feeding tube fastener of claim 10, wherein the lid is fastened to the base by fastening the side wall of the lid to the gripping aperture.

12. The feeding tube fastener of claim 10, wherein the lid of the feeding tube fastener comprises a pull tab for pulling the lid towards or away from the base of the feeding tube fastener.

13. The feeding tube fastener of claim 10, wherein the adhesive strip comprises polyurethane film.

14. The feeding tube fastener of claim 10, wherein the adhesive strip is configured to be applied on skin of a user, and wherein the adhesive strip is configured to provide a waterproof barrier to the skin of the user.

15. The feeding tube fastener of claim 10, wherein edges of the adhesive strip are rounded.

16. A method for holding a feeding tube comprising:
    inserting a portion of a feeding tube into a pair of grooves in a base of a feeding tube fastener, wherein the pair of grooves in the base extend across an entire length of the base;
    pulling a lid of a feeding tube fastener towards a base of the feeding tube fastener, wherein the base includes a gripping aperture positioned around an upper rim of the base, wherein a portion of the gripping aperture extends beyond an outermost edge of the base, wherein the lid comprises a side wall extending perpendicular to a smooth and flat top surface of the lid, wherein the side wall has a smooth interior and generally cylindrical shape, wherein the side wall includes two pairs of opposing grooves parallel to the pair of grooves in the base, wherein the top surface of the lid and the side wall have a circumference such that the side wall fastens to the gripping aperture;
    fastening the lid of the feeding tube fastener to the gripping aperture of the base by pushing the side wall of the lid against the gripping aperture such that the gripping aperture is in a vicinity of an intersection of the side wall and the top surface of the lid when the lid is closed over the base, wherein the two pairs of opposing grooves of the lid and the pair of grooves in the base are aligned and hold the feeding tube in place when the lid is fastened to the base; and
    applying the feeding tube fastener to skin of a user.

17. The method of claim 16, further comprising opening the feeding tube fastener by pulling a pull tab of the lid away from the base of the feeding tube fastener.

18. The method of claim 16, wherein the feeding tube fastener is applied to the skin of the user by utilizing an adhesive strip attached to a bottom surface of the base.

19. The method of claim 18, wherein the adhesive strip comprises polyurethane film.

20. The method of claim 16, wherein the lid is partially connected to the base by utilizing a connector.

\* \* \* \* \*